United States Patent [19]

Lerner

[11] Patent Number: 5,520,919
[45] Date of Patent: May 28, 1996

[54] VITAMIN A PALMITATE COMPOSITION AND METHODOLOGY FOR REPAIRING AND REJUVENATING HUMAN SKIN

[76] Inventor: Sheldon Lerner, 3399 First Ave., San Diego, Calif. 92103

[21] Appl. No.: 290,160

[22] Filed: Aug. 15, 1994

[51] Int. Cl.$^6$ .................................................. A61K 7/48
[52] U.S. Cl. ..................... 424/401; 514/772.6; 514/844; 514/846; 514/847
[58] Field of Search ........................... 424/401; 514/725, 514/772.1, 772.3, 772.6, 783, 786, 785, 941, 859, 844

[56] References Cited

U.S. PATENT DOCUMENTS 4,992,265  2/1991  Davis et al. ............................... 424/70
5,089,269  2/1992  Noda et al. ............................... 424/456
5,296,166  3/1994  Leong ........................................ 424/81

*Primary Examiner*—Thurman K. Page
*Attorney, Agent, or Firm*—Linda R. Neyenesch

[57] ABSTRACT

A topically administered composition and methodology of Vitamin A Palmitate for application with human skin care. The substance is composed of 4–10% A Palmitate in combination with at least 51% water surfactant. Non-irritating thickeners, preservatives and carriers synergize to achieve unrestricted topical application which repair and rejuvenate all of the layers of the skin tissue.

9 Claims, No Drawings

VITAMIN A PALMITATE COMPOSITION AND METHODOLOGY FOR REPAIRING AND REJUVENATING HUMAN SKIN

BACKGROUND OF THE INVENTION

1. Field of the Invention

The present invention relates to a Vitamin A palmitate composition and methodology for topical application to human skin. More specifically, the present invention cures a wide range of skin disorders such as acne, uneven pigmentation, photoaging, excessive accumulation of epidermal layers and repair of the entire dermal tissue without irritating side effects.

PRIOR ART

2. Description of the Prior Art

U.S. Pat. Nos. 5,043,356 (Fulton, Jr.); 3,906,108 (Felty); 4,532,133 (Schmidt); 4,603,146 (Kligman) and 4,727,088 (Scott et al) have been reviewed for purposes of the prior art search.

A wide range of factors contribute to the phenotype of damaged skin. These factors may take the form of environmental toxins (smoke, pollution, etc.,), sun damage, genetic disposition, susceptibility of fair skin, and age. As stated by the main reference, Fulton et al, the skin losses its ability to repair itself with age. Microscopic degradation becomes macroscopic, depending upon the combination of variables cited above which become manifested in early aging. These issues are non-disputed by the prior art patents.

Vitamin A is well known for its nutritional and therapeutic qualities, especially for the epithelia. Fulton discussed the internal use of Vitamin A palmitate in U.S. Pat. No. 5,043, 356. Although his research source is not well documented, Fulton alleges stimulation of new cell growth in the epithelium only, with adverse side effects resultant from Vitamin A toxic symptoms. Fulton further alleges that topical application of the Vitamin A palmitate molecule is too large to transdermally traverse the necessary part of the skin. The site of the skin which Fulton alludes to is unstated, nor is there reference to the non-irritating effects of Vitamin A Palmitate. The instant invention overcomes Fulton in many respects.

To begin with, the topical application of the palmitate A solution does not cause any known adverse side effects. Therefore, it can be administered freely and safely without burning the skin. Side effects associated with early research of internally administered A Palmitate (1940), such as headaches, migraine headaches, fatigue, bone pain, etc., further distinguish the instant invention. Topical treatment is an entirely different issue.

There is mounting evidence borne out by recent research and the instant inventor's reduction to practice of his composition and method of application that the molecule transcends the stratified epithelium to access the dermis. Not only does the composition exfoliate dead cornified layers, it reaches the mesenchyme, allowing repair, thickening, and proliferation of new cell layers as well as increased blood flow. Basal improvements are manifested in the epithelium which then becomes smoother and less pigmented. Yet another limitation of the A Palmitate experiments cited by Fulton may have been utilization of insufficient amounts of A palmitate. Schmidt (U.S. Pat. No. 4,532,133) discusses the instability of the Vitamin A molecule when exposed to air oxidation, heat and/or water prior to the addition to animal feed. As will be described, the instant invention has overcome these limitations and applied the improvement to human use.

The patent to Kligman (U.S. Pat. No. 4,603,146) utilizes a composition of Vitamin A acid (retionic acid). The patent describes a carefully monitored sub-irritating dose of the potentially harmful retionic acid. The instant invention overcomes Kligman on at least two points. Although Kligman discusses Vitamin A (acid) in an emollient vehicle, the dosage must be carefully monitored because of the harmful effects of this form of acid on the skin. The Palmitate A composition of the instant invention overcomes Kligman because it does not irritate the skin, even in its highest concentration. Nor does Kligman state in his singular main claim the proportions of A acid to emollient. He merely states that the dosage be sub-irritating. The method, means, maintenance therapy and composition are therefore extremely ambiguous if not totally absent from the invention as claimed.

Scott (U.S. Pat. No. 4,727,088) comprises a pharmaceutical preparation in the form of an antiperspirant stick in combination with a volatile alcohol and the retinoic acid form of Vitamin A for the treatment of acne. The limitations of the sub-irritating dosage problems have been discussed above, especially with respect dosage problems have been discussed above, especially with respect to the Kligman patent. Felty (U.S. Pat. No. 3,906,108) also utilizes the potentially harmful retinoic acid in yet another emulsion (xanthan gum, et al) for purposes of enhanced shelf-life and stability.

Until the emergence of the present invention, there has been no safe and effective means of treating skin disorders and aging with topical application.

SUMMARY OF THE INVENTION

This invention is directed to the treatment of physiologic conditions commonly associated with aging of human skin. These morphological symptoms include visibile wrinkles, leatheriness, roughness, dryness, skin looseness, loss of elasticity, pronounced pigment variations and lesions. Accompanying these symptoms are reduced cell development and exfoliation with a thickened epidermal layer. The foregoing conditions are mirrored in the condition of the underlying dermis. The supporting fascicular and soluble collagen and elastin fibers lose support for the epidermis. Mechanical and nutritive support for the epidermis thus diminishes.

The invention is based upon the discovery that sufficient amounts of Vitamin A Palmitate in combination with a specific composition achieves bioavailability of the A molecule in the dermis and epidermis. Besides the superior penetration qualities of the A composition, there is also mounting evidence that the stratified epidermis displays a coordinated response from a factor signaling pathways are generated low in the basal layer and induce a molecular signal for cell proliferation throughout the companion dermal tissue. Years of research by the instant inventor have culminated in a product that accesses the dermis in combination with a synergism of appropriate carriers of the A molecule and the physiological mechanism of molecular signaling. This synergism is readily apparent when the skin is viewed as a viable and dynamic organ, interacting as a whole. An additional aspect of the present invention is the absence of irritating side effects which make possible a more liberal method of topical application and enhanced repair time of skin tissue.

DETAILED DESCRIPTION OF THE INVENTION

Without limiting the scope of the invention, preferred method or preparing the composition is set forth below:

The method for preparing the composition of claim 1 including the following steps:
 to 60 grams of deionized water, add 30 grams of carboxyvinyl polymers in a 1.5 wt/% solution;
 add five gram of polyoxyethylene;
 heat to 160 F;
 to the above composition ad six grams of vitamin A palmitate, two grams of sorbitan sesquioleate, 0.5 grams of urea, inositol, sodium lactate, sodium PCA padimate, niacinamide, phenoxyethanol, lactic acid, methylparaben, propylparaben and 0.1 grams of BHT, sodium benzoate an citric acid;
 mix the solution while cooling to 110 F and add 5 grams of aloe vera; and
 mix the viscosity to 25,000 cPs using a viscometer and add 10% solution of sodium hydroxide.

The therapeutic component of the Vitamin A Palmitate molecule is distinguished from other derivatives of Vitamin A, as follows:

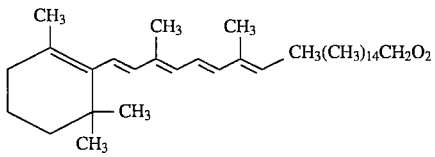

The limitations of topical treatment with other forms of vitamin A have been discussed in the prior art portion of this application. The following description sets forth the substantial improvement over the prior art and its effectiveness in harnessing Vitamin A Palmitate, the safest and most effective modulator of growth and regeneration.

Without limiting the scope of the invention and for purposes of illustration, the aqueous base composition of the present invention for application to human skin is described as follows. Vitamin A Palmitate is carried by a water surfactant in the approximate solution of 51%. The percentage of A Palmitate to water has been found effective in the range of 4–10% In contrast to other carriers in the prior art which bind the A molecule and reduce its bioavailability, the water evaporates, thus allowing the Vitamin A its maximum exposure to access the dermal layers. The water slurry also contains Carbomer 940 solution, Glycereth 26 and Sorbitan Sesquioleate. In combination, these inert substances comprise a non-irritating suspension. Aloe Vera comprises a small percentage for an overall soothing application of the product.

Preservation and stabilization are achieved by the inclusion of phenoxyethanol, methylparaben, propylparaben, yet another improvement over prior art limitations.

Topical application of the A Palmitate composition achieves rejuvenation and healing of the total dermal organ without adverse side effects. As stated hereinbefore, undesirable skin conditions take the form of acne, damaged basal membranes, excessive accumulation of epidermal layers, photoaging, and uneven pigmentation. The pathology of skin disorders is infinite; however, the instant invention has reduced to practice a composition and method which cure and/or mitigate a large number of them. The results are exhibited by exfoliation of dead, cornified layers, access to the basal tissue, repair, thickening and proliferation of new cell layers, as well as increased blood flow. Morphological improvement has been observed in the young, proliferating dermis and there is clear evidence that the instant composition displays evidence of accessing the basal layer by means of its superior penetration qualities in combination with stimulation of growth factor signaling pathways within the total epithelia.

The composition has proved equally effective with varying skin types of pigment and oil production. Because of its non-irritating qualities, the application does not comprise a pharmaceutical substance which requires monitoring or prescription. The human research subjects used the composition liberally and none of the irritating side effects of Vitamin A acid were observed. The percentages in the data of low improvement indicated improper application procedures. These experiments are current and in-progress.

EXAMPLE 1

Preparation of a Water Based Composition in Combination with Vitamin A Palmitate for Treating Skin Disorders One hundred patients between the ages of thirty-five and sixty applied Vitamin A Gel in the solution described for a period of six months. Applications were made once daily following a cleansing and defatting of the skin. At the end of three months 82% showed noticeable improvement in overall skin conditions. These improvements included a reduction in hyperpigmentation, improved clarity and firmer skin tone.

At the end of six months 91% showed improvement in overall skin conditions, and the majority of subjects exhibited significant improvement in skin firmness and reduction of noticeable lines and wrinkles. The remainder of patients showing little improvement indicated deviation from the research protocol.

EXAMPLE 2

Preparation of a Water Based Composition in combination with Vitamin A Palmitate for Treating Skin Disorders Fifty patients between the ages of thirty-five and sixty applied Vitamin A Gel in the solution described and applications of at least 4% glycolic cleanser, 15% glycolic toner and 10% glycolic lotions. Applications of Vitamin A Gel were made once daily in the morning following cleansing and defatting of the skin; applications of the glycolic products were made once daily in the evening.

At the end of three months 86% exhibited noticeable improvement in overall skin conditions. These improvements included reduction in hyperpigmentation, improved clarity and firmer skin tone. Patients in this group exhibited significant mitigation of hyperpigmentation than the control group of Example 1.

At the end of six months 93% manifested clear clinical evidence of improvement in overall skin conditions and the majority evidence of improvement in overall skin conditions and the majority of subjects showed marked improvement in firmness, reduction of noticeable lines, and wrinkles. Firmness and migitation of lines was more noticeable than in Example 1 and skin clarity was greatly enhanced. The remaining 7% indicated deviation from the experiment protocol.

EXAMPLE 3

Preparation of a Water Based Composition in Combination with Glycolic Cleanser, Toner and Lotion for Treatment of Skin Disorders Fifty patients between the ages of thirty-five and sixty applied 4% glycolic cleanser, 15% glycolic toner and 10% glycolic lotion for a period of six months. Applications were made once daily. At the end of three months, 86% exhibited improvements in skin conditions; however, the majority had improvement in hyperpigmentation only.

At the end of six months 88% showed overall improvement of skin conditions. Improvement in hyperpigmentation was equal to Examples 1 and 2. Improvement in noticeable lines and wrinkles was less than Examples 1 and 2. Improvement in skin firmness occurred in few patients and could be attributed to a general improvement in skin care practices.

As can be seen from the above examples, the preferred Example 3 has been included for purposes of omitting the A composition and, although there was noticeable improvement, Examples 1 and 2 clearly establish the effectiveness of the Palmitate A topical treatment.

While there have been shown and described the preferred embodiment of the Palmitate A composition and its application, it will be appreciated that changes and alterations may be made therein without departing from the spirit and scope of the essential spirit of the invention.

What is claimed is:

1. A topically applied composition for repairing and improving the health of human skin having enhanced bioavailability comprising:

from 4% to 10% Vitamin A Palmitate;

a minimum of 51% water;

a minimum of 25% carboxyvinyl polymers;

4% Aloe Vera;

4% of a polyoxyethlene;

2% sorbitan sesquioleate.

2. The composition of claim 1 and further including preservatives selected from the group consisting of phenoxyethanol, methylparaben and propylparaben.

3. The composition of claim 1 wherein the carboxyvinyl polymers act to hold said composition in suspension.

4. The composition of claim 1 wherein topical application is carried into the skin by the water based surfactant which evaporates upon application, effecting penetration of the A Palmitate composition to the lowest dermal layers distal to the stratum corneum.

5. The composition of claim 1 wherein said Vitamin A Palmitate is less irritating in the respective concentration in combination with a high water ratio.

6. The composition of claim 1 wherein said Vitamin A Palmitate in combination with its carriers stimulate growth in the basal cell layer.

7. The composition of claim 1 wherein exfoliation of human skin is achieved without irritating side effects or pain.

8. The composition of claim 1 wherein hyperpigmentation is mitigated or eradicated.

9. A method for application of the Vitamin A Palmitate composition of claims 1, 2 or 3 comprising:

cleansing and defatting of the skin thoroughly before application in the morning and evening; and application of composition immediately after cleansing and defatting.

* * * * *